United States Patent [19]

Kato et al.

[11] Patent Number: 5,235,091

[45] Date of Patent: Aug. 10, 1993

[54] PROCESS FOR PREPARING DIPHENYLMETHANE COMPOUNDS

[75] Inventors: Masayasu Kato, Ashiya; Toru Ishida, Takarazuka, both of Japan

[73] Assignee: Takeda Chemical Industries, Ltd., Osaka, Japan

[21] Appl. No.: 959,604

[22] Filed: Oct. 13, 1992

[30] Foreign Application Priority Data

Oct. 15, 1991 [JP]  Japan .................................. 3-266338

[51] Int. Cl.$^5$ .................................................. C07C 69/76
[52] U.S. Cl. ...................................... 560/57; 562/491; 568/640; 568/744; 564/171
[58] Field of Search ............................ 560/57; 562/491

[56] References Cited

U.S. PATENT DOCUMENTS 3,954,839  5/1976  Dexter et al. ........................ 560/57

FOREIGN PATENT DOCUMENTS 58-83640  5/1983  Japan .
61-44840  3/1986  Japan .
2-152940  6/1990  Japan .

OTHER PUBLICATIONS

Ansell et al., Jour. Chem. Soc., Perkin Transactions I (1973) pp. 2789-2795.

Coscia et al., J. Org. Chem., vol. 26 (1961) pp. 1398-1401.

*Primary Examiner*—Paul J. Killos
*Attorney, Agent, or Firm*—Wenderoth, Lind & Ponack

[57] ABSTRACT

A diphenylmethane compound (III) can be produced in a good yield by allowing a phenol compound (I) to react with a stilbene compound (II) in the presence of methanesulfonic acid

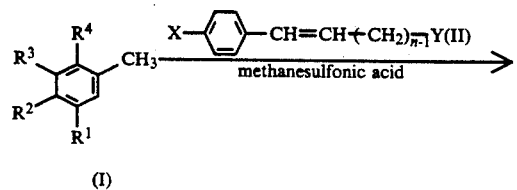

(I)

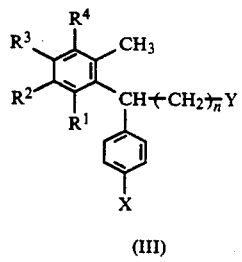

(III)

4 Claims, No Drawings

PROCESS FOR PREPARING DIPHENYLMETHANE COMPOUNDS

This invention relates to a process for preparing diphenylmethane compounds which are themselves useful in preparing a phenol derivative or a hydroquinone derivative thereof useful for the treatment or prophylaxis of cerebral, cardiac, renal and pulmonary circulatory disturbances, diseases of the respiratory system, allergy, anaphylactic shock, inflammatory diseases, etc.

The above-mentioned phenol derivative and hydroquinone derivative are disclosed in, for example, JPA S61(1986)-44840 and JPA H2(1990)-152940. These compounds are synthesized from diphenylmethane compounds represented by the general formula:

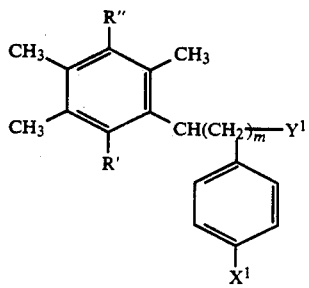
(a)

[wherein R' is an optionally protected hydroxyl, R" is hydrogen or an optionally protected hydroxyl, X¹ is a halogen, a lower alkyl or a lower alkoxy, Y¹ is methyl, an optionally substituted hydroxymethyl or an optionally esterified or amidated carboxyl, and m is an integer of 3 to 15]. It is disclosed that these compounds represented by (a) can be produced by allowing a compound of the formula:

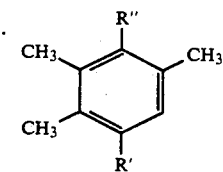
(b)

[wherein each symbol has the same meaning as defined above] to react with a compound of the formula:

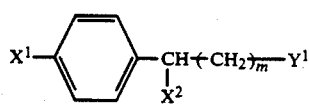
(c)

[wherein X¹, Y¹ and m have the same meaning as defined above, X² is hydroxyl, acetoxy, a lower alkoxy or a halogen].

However, for producing the above compound (c), 4 to 5 steps are required, and, besides, the yield is low. Therefore, development of an industrially advantageous process of producing said compound has been desired. The present inventors diligently studied on these points and found that the diphenylmethane compounds (a) can be prepared in a good yield by allowing the above-mentioned compound (b) to react with a stilbene derivative, which can be readily produced, in the presence of a specific acid catalyst.

The present invention thus relates to a process of preparing a diphenylmethane compound of the formula:

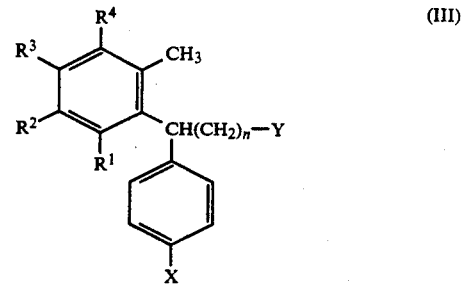
(III)

[wherein R¹ is an optionally protected hydroxyl, R² and R³ each is methyl or methoxy, R⁴ is hydrogen or an optionally protected hydroxyl, Y is methyl, an optionally esterified or amidated carboxyl, and n is an integer of 1 to 15], which comprises reacting a phenol compound of the formula:

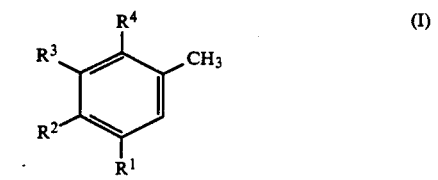
(I)

[wherein the symbols have the same meaning as defined above] with a stilbene compound of the formula:

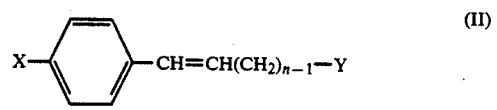
(II)

[wherein X is hydrogen, a halogen, a lower alkyl or a lower alkoxy, and the other symbols have the same meaning as defined above] in the presence of methanesulfonic acid.

In the above formulas (I) and (III), examples of the optionally protected hydroxyl shown by R¹ or R⁴ include hydroxyl, a lower alkoxy (e.g., a $C_1$-$C_4$ one such as methoxy, ethoxy or propoxy), methoxymethyloxy, benzyloxy, a lower acyloxy (e.g., a $C_1$-$C_4$ one such as formyloxy, acetoxy or propionyloxy), and tetrahydropyranyloxy.

In the above formulas (I) and (III), R² and R³ are methyl or methoxy, preferably methyl.

In the above compounds (II) and (III), examples of halogen shown by X include fluorine, chlorine and bromine.

In the compounds (II) and (III), hydroxymethyl shown by Y is optionally O-substituted, and examples thereof include, besides an unsubstituted hydroxymethyl, an O-substituted one on its hydroxyl, such as methoxymethyl, acetoxymethyl, 2-tetrahydropyranyloxymethyl, benzyloxymethyl, nitroxymethyl, aminocarbonyloxymethyl, substituted aminocarbonyloxymethyl (e.g. methylaminocarbonyloxymethyl, ethylaminocarbonyloxymethyl, dimethylaminocarbonyloxymethyl, phenylaminocarbonyloxymethyl), a cyclic aminocarbonyloxymethyl (e.g. morpholinocarbonyloxymethyl, pyrrolidinocarbonyloxymethyl, piperazinocarbonyloxymethyl), and t-butyl dimethylsilyloxymethyl; and examples of the esterified carboxyl include $C_2$-$C_4$ alkoxycarbonyl such as methoxycarbonyl, ethoxycarbonyl. The amidated carboxyl shown by Y may be an aminocarbonyl substituted on its amino group or a cyclic aminocarbonyl. Examples of the substituents on amino group of the substituted aminocarbonyl include $C_1$-$C_4$ alkyl such as methyl, ethyl, propyl, isopropyl or butyl, $C_6$-$C_{10}$ aryl such as phenyl or naphthyl (these groups may have further substituents on an optional position of the ring, such as hydroxyl, amino, nitro, halogen, methyl or methoxy), and hydroxyl. Practical examples of the amidated carboxyl include aminocarbonyl, mono- or di-alkylamino-carbonyl (whose mono or di-alkyl moiety is one having 1 to 4 carbon atoms such as methylamino, ethylamino, isopropylamino, dimethylamino), an aralkylaminocarbonyl [whose aralkyl amino moiety includes benzylamino, α-phenethylamino, β-phenethylamino, 1-(α-naphthyl)ethylamino], phenylaminocarbonyl, substituted phenylaminocarbonyl (whose substituted phenylamine includes p-hydroxyphenylamino, p-methoxyphenylamino, m-chlorophenylamino, p-bromophenylamino), diphenylaminocarbonyl, hydroxyaminocarbonyl, N-hydroxy-N-methylaminocarbonyl, and N-hydroxy-N-phenylaminocarbonyl. The cyclic aminocarbonyl is 5 or 6 membered ring-carbonyl which may have oxygen and/or sulfur other than nitrogen as a ring constituting atom, and which includes morpholinocarbonyl, thiomorpholino-carbonyl, piperidinocarbonyl and pyrrolidinocarbonyl.

In the above-mentioned formulas (II) and (III), n is an integer of 1 to 15, preferably 2-13, more preferably 3 to 10.

In the reaction of this invention, the compound (II) is used, relative to one mol. of the compound (I), in a range of from about 0.5 to 1.5 mol., preferably from 0.75 to 1.25 mol., especially preferably from 0.9 to 1.1 mol.

The molar amount of methanesulfonic acid used in the reaction is in the range of 0.5 to 20 times as much as the molar amount of compound (I). Preferably the amount is 1 to 10, or especially preferably 2 to 5 times, as much as the molar amount of compound (I).

Examples of the solvent to be employed for the reaction include a non-polar solvent such as methylene chloride, chloroform, 1,2-dichloroethane, 1,1,2-trichloroethane, benzene or toluene, preferably methylene chloride, chloroform or 1,2-dichloroethane. Especially methylene chloride is preferably employed. These solvents can be used singly or as a mixture of them. The volume of these solvents to be used ranges usually from about 0.5 to 10 liters relative to one mol. of the compound (III), preferably 1 to 5 liters, but is not limited to this range.

The reaction is conducted, for preventing polymerization of the compound (II), usually at a temperature lower than those in conventional Friedel-Craft reactions, more specifically, usually those ranging from about $-20°$ to $50°$ C., preferably from about $-5°$ to $35°$ C.

The reaction time ranges usually from about 0.5 to 24 hours, preferably from about 1 to 8 hours.

The object compound (III) prepared by the above-mentioned reaction, when precipitated as crystals from the reaction mixture, can be isolated by collecting the crystals by filtration, and, when necessary, the reaction mixture may be subjected to extraction with a solvent, for example, methylene chloride, then the extract is concentrated to isolate the object compound. In the case where no precipitation of crystals occurs from the reaction mixture, the reaction mixture may be subjected to extraction with a solvent, for example, methylene chloride, then the extract is concentrated to isolate the object compound.

The crystals thus isolated can be refined, upon necessity, by a conventional means such as recrystallization or chromatography.

The starting compound (I) is a known one or can be produced by a known method. The starting compounds (II) are partially known compounds. For example, a compound (II), wherein Y is carboxyl group, can be obtained by allowing a compound of the formula:

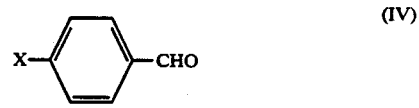

(IV)

wherein X has the same meaning as defined above] to react with a compound of the formula:

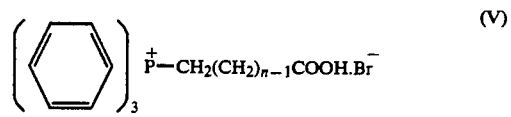

(V)

[wherein n has the same meaning as defined above.] This reaction is conducted usually in a solvent such as isopropanol, isobutanol, tertiary butanol, ether or tetrahydrofuran in the presence of a metallic hydride such as sodium hydride or a tertiary alkoxide of an alkali metal such as sodium tertiary butoxide, potassium tertiary butoxide. Then, upon necessity, by converting the carboxylic acid in accordance with a known method, the compound (III) can be produced.

The final compound (III) of this invention, wherein both $R^1$ and $R^4$ are hydroxyl group, possesses medicinal effects itself (cf. JpA S61(1986)-44840).

The compounds (III), wherein $R^1$ and/or $R^4$ is a protected hydroxyl, can be transformed to those wherein $R^1$ and/or $R^4$ is hydroxyl by means of a conventional deprotection. The compound (III), wherein $R^1$ is hydroxyl group and $R^4$ is hydrogen or hydroxyl group, can be transformed to a quinone compound of the formula:

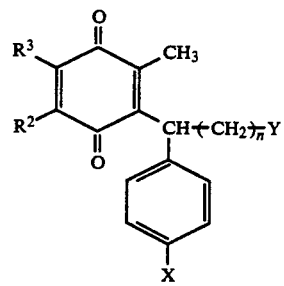

[wherein each symbol has the same meaning as defined above], which have pharmacological actions, by subjecting the former to conventional oxidation (cf. JPA S61(1986)-44840).

And, the compound (III), wherein $R^4$ is hydrogen, can be transformed to a compound of the formula:

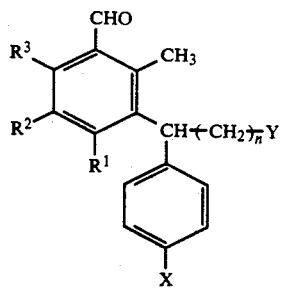

[wherein each symbol has the same meaning as defined above], which has pharmacological actions, by formylation (cf. JPA H2(1990)-152940), and, the latter compound can be transformed to a compound of the formula:

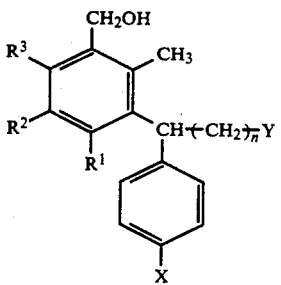

[wherein each symbol has the same meaning as defined above], which has pharmacological action, by further subjecting the compound to reduction (cf. JPA H2(1990)-152940).

According to the method of this invention, the desired intermediates can be produced in a good yield by employing starting materials which can be easily produced.

The following working examples, reference examples and comparative examples will describe the present invention in more detail.

REFERENCE EXAMPLE 1 (PRODUCTION OF 7-PHENYL-6-HEPTENOIC ACID)

5-Carboxypentyl-triphenylphosphonium bromide (20 g) and benzaldehyde (5.6 g) were suspended in isopropanol (100 ml). To the suspension was added potassium butoxide (10.8 g) in limited amounts at 25° C., then the reaction was allowed to proceed for 2 hours at 70° C. Isopropanol was distilled off under reduced pressure. To the residue was added water (100 ml) to make a solution, which was acidified with hydrochloric acid, followed by extraction with ethyl acetate. The extract was washed with water, dried and concentrated under reduced pressure. The concentrate was subjected to a silica gel column chromatography to afford 7-phenyl-6-heptenoic acid (7.6 g) as a colorless oily product.

NMR spectrum ($\delta$ value determined with use of TMS as the standard in deuterium chloroform): 1.30–2.50(8H), 5.50–6.55(2H), 7.28(5H)

REFERENCE EXAMPLE 2 (PRODUCTION OF 7-(4-FLUOROPHENYL)-6-HEPTENOIC ACID)

5-Carboxypentyl-triphenylphosphonium bromide (20 g) and 4-fluorobenzaldehyde (6.5 g) were subjected to substantially the same reaction as in Reference Example 1. The reaction product was isolated by means of a silica gel chromatography to afford 7-(4-fluorophenyl)-6-heptenoic acid (8.3 g) as white crystals.

NMR spectrum ($\delta$ value determined with the use of TMS as the standard in deuterium chloroform): 1.20–2.55(8H), 5.91–6.56(2H), 6.80–7.50(4H)

EXAMPLE 1 (PRODUCTION OF COMPOUND 1)

7-Phenyl-6-heptenoic acid (10 g) obtained in accordance with the procedure described in Reference Example 1 and 2,3,5-trimethyl-1,4-hydroquinone (5.6 g) were suspended in dichloromethane. To the suspension was added dropwise methanesulfonic acid (9.6 g) at a temperature ranging from 25° to 30° C. The mixture was stirred at 25° C. for 5 hours, to which was then added water (41 ml). Resulting crystalline precipitates were collected by filtration, washed with dichloromethane and water successively, then dried under reduced pressure to give 7-(3,5,6-trimethyl-1,4-hydroquinon-2-yl)-7-phenylheptanoic acid (13.4 g, yield 76.7%):

7-(3,5,6-Trimethyl-1,4-hydroquinon-2-yl)-7-phenylheptanoic acid (13.4 g) was dissolved in 86% acetonitrile (water content: 14%). To the solution was added 34 ml of a 38% aqueous solution of ferric chloride, and the mixture was stirred at 70° C. for one hour. The reaction mixture was cooled with ice to cause precipitation of crystals. The crystals were collected by filtration and recrystallized from 60% acetonitrile (water content: 40%) to afford 7-(3,5,6-trimethyl-1,4-benzoquinon-2-yl)-7-phenylheptanoic acid (12.0, g, yield from hydroquinone: 90.2%, yield from heptenoic acid: 69.2%) as yellow crystals

[Since 7-(3,5,6-trimethyl-1,4-hydroquinon-2-yl)-7-phenylheptanoic acid is subject to oxidation and may be partially transformed into 7-(3,5,6-trimethyl-1,4-benzoquinon-2-yl)-7-phenylheptanoic acid, the oxidation reaction is included in Examples.]

In substantially the same manner as above, Compounds 2 to 9 can be produced.

TABLE 1

| Compound No. | X | Y | n | Molecular Formula | Melting Point (°C.) |
|---|---|---|---|---|---|
| 1 | H | COOH | 5 | $C_{22}H_{26}O_4$ | 128–129 |
| 2 | H | COOH | 4 | $C_{21}H_{24}O_4$ | 125–126 |
| 3 | H | COOH | 6 | $C_{23}H_{28}O_4$ | 94–95 |
| 4 | H | COOEt | 4 | $C_{23}H_{28}O_4$ | oil |
| 5 | H | COOMe | 8 | $C_{26}H_{34}O_4$ | oil |
| 6 | H | $CH_2OCONH_2$ | 4 | $C_{22}H_{27}NO_4$ | 125–126 |
| 7 | H | $CH_2OCONHMe$ | 4 | $C_{23}H_{29}NO_4$ | 135–136 |
| 8 | Cl | COOH | 5 | $C_{22}H_{25}ClO_4$ | 142–143 |
| 9 | Br | COOH | 5 | $C_{22}H_{25}BrO_4$ | 148–150 |

EXAMPLE 2 (PRODUCTION OF COMPOUND 10)

7-(4-Fluorophenyl)-6-heptenoic acid (10.0 g) obtained in accordance with the procedure described in Reference Example 2 and 2,3,5-trimethyl phenol (9.0 g)

were dissolved in dichloromethane (200 ml). To the solution was added dropwise methanesulfonic acid (43.3 g) at a temperature ranging from 2° to 5° C. The reaction mixture was stirred at 2° to 3° C. for 3 hours, to which was added water (100 ml). The dichloromethane layer was separated and washed with water three times. Dichloromethane was distilled off under reduced pressure, then the residue was subjected to a silica gel chromatography to thereby afford 7-(4-fluorophenyl)-7-(2-hydroxy-3,4,6-trimethylphenyl)heptanoic acid (12,7 g, 79.0%) as white crystals.

In substantially the same manner as above, Compounds 11 to 12 can be produced.

TABLE 2

[Structure: trimethylphenyl group with R⁴, R¹, CH₃ groups and CH(CH₂)ₙY attached to phenyl ring with X substituent]

| | R¹ | R⁴ | X | Y | n | Molecular Formula | Melting Point (°C.) |
|---|---|---|---|---|---|---|---|
| 10 | OH | H | F | COOH | 5 | $C_{22}H_{27}FO_3$ | 128–129 |
| 11 | OH | H | F | COOEt | 5 | $C_{24}H_{31}FO_3$ | oil |
| 12 | OH | OMe | F | COOMe | 5 | $C_{24}H_{31}FO_3$ | oil |

REFERENCE EXAMPLE 3

To a solution of 7-(4-fluorophenyl)-7-(2-hydroxy-3,4,6-trimethylphenyl)heptanoic acid (10.0 g) obtained in accordance with the procedure described in Example 2 and dichloromethyl methylether (6.0 ml) in dichloromethane (100 ml) was added dropwise titanium tetrachloride (19.2 ml) at a temperature ranging from −14° to −9° C. While the reaction mixture was kept at −10° C., it was stirred for 30 minutes, to which was poured ice-water (100 ml), followed by stirring vigorously. The dichloromethane layer was separated, washed with water and dried. It was then subjected to concentration under reduced pressure. The concentrate was recrystalized from a mixture of tetrahydrofuran and isopropyl ether to afford 7-(4-fluorophenyl)-7-(5-formyl-2-hydroxy-3,4,6-trimethylphenyl)heptanoic acid (9.92 g).

NMR spectrum (δ value determined with the use of TMS as the standard in deuterium chloroform): 1.04–2.60(10H), 2.10(3H), 2.45(3H), 2.53(3H), 4.56(1H), 6.82–7.36(4H), 10.58(1H)

REFERENCE EXAMPLE 4

To a solution of 7-(4-fluorophenyl)-7-(5-formyl-2-hydroxy-3,4,6-trimethylphenyl)heptanoic acid (5.0 g) obtained in accordance with the procedure described in Reference Example 3 in tetrahydrofuran (50 ml) was added sodium borohydride (0.25 g) at 2° C., and the mixture was stirred for one hour. To the reaction mixture were added ethyl acetate and water. The mixture was stirred, then the organic layer was separated and washed with water twice. The organic layer was dried over magnesium sulfate, which was concentrated under reduced pressure. The concentrate was recrystallized from tetrahydrofuran-acetonitrile to afford 7-(4-fluorophenyl)-7-(2-hydroxy-5-hydroxymethyl-3,4,6-trimethylphenyl)heptanoic acid (4.5 g).

NMR spectrum (δ value determined with the use of TMS as the standard in DMSO-d₆): 0.96–1.55(6H), 1.98–2.30(4H), 2.07(3H), 2.21(6H), 4.15–4.83(4H), 7.01(2H), 7.21(2H), 7.82(1H), 11.94(1H)

EXAMPLE 3 (PRODUCTION OF 7-(2-HYDROXY-3,4,6-TRIMETHYLPHENYL)-7-PHENYLHEPTANOIC ACID)

7-Phenyl-6-heptenoic acid (10 g) and 2,3,5-trimethylphenol (8.3 g) were suspended in dichloromethane (80 ml). To the suspension was added dropwise methanesulfonic acid (9.4 g) at a temperature ranging from 17°–25° C. The mixture was stirred at 25° C. for 6 hours, to which was then added water (80 ml). The dichloromethane layer was separated and washed with water three times. Dichloromethane was distilled off under reduced pressure, and the residue was recrystallized from toluene (38 m;) to give 7-(2-hydroxy-3,4,6-trimethylphenyl)-7-phenylheptanoic acid (14.2g, 85.2%) as white crystals.

REFERENCE EXAMPLE 5

7-(2-hydroxy-3,4,6-trimethylphenyl)-7-phenylheptanoic acid (5.0 g) was dissolved in a mixed solution of acetonitrile (25 ml), water (10 ml) and 25% aqueous ammonia (1 ml), to which 3% aqueous solution (280 ml) of potassium nitrosodisulfonate (Fremy's salt) was added. The mixture was stirred at a temperature of 2° to 4° C. for 2 hours. The reaction mixture was acidified with hydrochloric acid, followed by extraction with ethyl acetate. The ethyl acetate layer was washed with water twice. Ethyl acetate was distilled off under reduced pressure, and the residue was recrystalized from a mixed solution of acetonitrile and water (6:4) to give 7-(3,5,6-trimethyl-1,4-benzoquinone-2-yl)-7-phenylheptanoic acid (4.90 g, 94.1%) as yellow crystals.

COMPARATIVE EXAMPLE 1

7-Phenyl-6-heptenoic acid (4.7 g), 2,3,5-trimethyl hydroquinone (5.6 g) and p-toluenesulfonic acid (18.6 g) were dissolved in 1,2-dichloroethane (94 ml), and the solution was stirred at 82°–83° C. for one hour. The solvent was distilled off under reduced pressure, and the residue was dissolved in ethyl acetate (100 ml). The solution was washed with water (50 ml) three times. Ethyl acetate was distilled off under reduced pressure. The residue was subjected to a silica gel chromatography to afford 7-(3,5,6-trimethyl-1,4-hydroquinon-2-yl)-7-phenyl heptanoic acid (1.5 g, yield 18%).

In substantially the same manner as above, reactions were attempted under the following conditions, but in no cases was the end product obtained.

| Reaction Conditions | | | |
|---|---|---|---|
| Acid | Solvent | Temp. (°C.) | Results |
| $H_2SO_4$ | $CH_2Cl_2$ | 40 | No end product obtained (Black tar-like substance was produced) |
| $AlCl_3$ | " | 25 | Polymer of 7-phenyl-6-heptenoic acid |
| $SnCl_4.H_2O$ | " | " | No reaction occurred |
| $BF_3.Et_2O$ | " | " | No reaction occurred |

We claim:
1. A process of preparing a diphenylmethane compound of the formula:

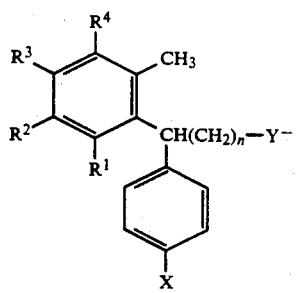

wherein R¹ is an optionally protected hydroxyl, R² and R³ each is methyl or methoxy, and R⁴ stands for hydrogen or an optionally protected hydroxyl, Y is methyl group, an optionally O-substituted hydroxymethyl or an optionally esterified or amidated carboxyl, and n is an integer of 1 to 15, which comprises reacting a phenol compound of the formula:

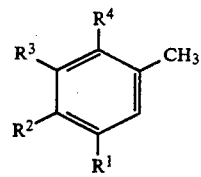

wherein the symbols have the same meaning as defined above with a stilbene compound of the formula:

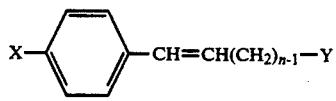

wherein X is hydrogen, a halogen, a lower alkyl or a lower alkoxy, and other symbols have the same meaning as defined above in the presence of methanesulfonic acid.

2. A process as claimed in claim 1, wherein the reaction is conducted at a temperature ranging from −20° C. to 50° C.

3. A method as claimed in claim 1, wherein the stilbene compound is used, relative to one mol. of the phenol compound, in a range of from about 0.5 to 1.5 mol.

4. A method as claimed in claim 1, wherein the molar amount of methanesulfonic acid used in the reaction is in the range of 0.5 to 20 times as much as the molar amount of the phenol compound.

* * * * *